(12) United States Patent
Arita

(10) Patent No.: US 6,660,194 B1
(45) Date of Patent: Dec. 9, 2003

(54) PROCESS FOR THE PREPARATION OF DENTAL PROSTHESIS

(75) Inventor: Akishi Arita, Tokyo (JP)

(73) Assignee: GC Corporation, Tokyo (JP)

( * ) Notice: Subject to any disclaimer, the term of this patent is extended or adjusted under 35 U.S.C. 154(b) by 182 days.

(21) Appl. No.: 09/705,754

(22) Filed: Nov. 6, 2000

(30) Foreign Application Priority Data

Nov. 10, 1999 (JP) ............................................. 11-319867

(51) Int. Cl.[7] ............................................... B29C 45/00
(52) U.S. Cl. ............................. 264/17; 264/16; 264/19; 425/2; 425/175
(58) Field of Search ............................. 264/16, 17, 19; 425/2, 175

(56) References Cited

U.S. PATENT DOCUMENTS

| | | | |
|---|---|---|---|
| 4,265,669 A | * | 5/1981 | Starling et al. ............. 501/153 |
| 5,502,087 A | * | 3/1996 | Tateosian et al. ......... 433/168.1 |
| 5,990,195 A | | 11/1999 | Arita |
| 6,186,761 B1 | * | 2/2001 | Petkow et al. ............... 425/178 |
| 6,335,385 B2 | * | 1/2002 | Gorlich et al. ................ 264/17 |
| 6,386,865 B1 | * | 5/2002 | Suh et al. ..................... 264/16 |

* cited by examiner

*Primary Examiner*—Jill L. Heitbrink
*Assistant Examiner*—Monica A Fontaine

(57) ABSTRACT

A process for preparing a dental prosthesis is disclosed, including preparing a wax pattern of an objective dental prosthesis based on a duplicated model having an intraoral shape, investing the wax pattern in an investment material, and removing the wax pattern to prepare a mold, wherein a composite resin is charged under pressure into the mold, and the composite resin is cured under heat and pressure, the process of the present invention enables one to obtain a dental prosthesis that has suitable esthetics and superior mechanical properties and free from fear of pulp irritation by the unpolymerized monomer, and particularly suitable for the preparation of inlays, crowns, etc.

8 Claims, No Drawings

PROCESS FOR THE PREPARATION OF DENTAL PROSTHESIS

BACKGROUND OF THE INVENTION

1. Field of the Invention

The present invention relates to a process for preparing a dental prosthesis from a composite resin.

2. Description of the Conventional Art

As the restoration of teeth are generally carried out by a restoration method using a dental prosthesis, in which, after preparation of a cavity, or after core construction of an abutment tooth, an impression (counterdie of tooth) is taken, a gypsum model (duplicate of tooth) is prepared based on the impression by using a gypsum or the like, a dental prosthesis is prepared based on the cast in a manner as described later, and the dental prosthesis is cemented to a tooth by using an adhesive such as a dental cement; and by a method of filling restoration, in which a dental composite resin is directly filled in a cavity and then polymerized and cured by chemical polymerization or light-polymerization to effect restoration.

In the case of dental prostheses such as inlays and crowns, there is widely employed a method called as a lost wax casting process, in which a dental wax is applied on a gypsum model to prepare a wax pattern having the same shape as an objective dental prosthesis; the wax pattern is invested in a refractory investment; after setting the investment, the wax pattern is heated and burnt in an electric furnace; a dental alloy is cast using a cast molding thus obtained; and the resulting cast material is excavated from the investment, followed by triming and polishing to prepare a metallic dental prosthesis.

In cases of inlays, crowns, etc., particularly in cases where aesthetics in, for example, restoration of anterior teeth, are required, restoration by means of dental prostheses such as ceramic inlays, resin facing crowns, porcelain facing metal crowns, and all ceramic crowns is carried out.

Specifically, in the case of dental prostheses such as ceramic inlays and all ceramic crowns, a refractory duplicated model is prepared by using a refractory material, a dental ceramics powder is built up and formed on the refractory duplicated model through manual works by a dental technician, and after firing, the refractory duplicated model is removed, followed by forming the surface characterization and polishing to prepare a dental prosthesis. Further, in the case of resin facing crowns or porcelain facing metal crowns, a resin having a tooth crown color is built up and polymerized for application on a labial surface of a metal crown prepared by the lost wax casting process, or a porcelain having a tooth crown color is built up and fired and then subjected to forming the surface characterization and polishing, to prepare a dental prosthesis.

However, in the case of dental filling restoration using composite resins, since the dental composite resin is filled in a cavity and immediately thereafter polymerized and cured, the strength is often insufficient. Further, since the unpolymerized monomer likely remains, a problem of pulp irritation is also pointed out. In addition, in the case of metallic dental prostheses, since a metal color is exposed on a surface of the dental prosthesis, a problem of aesthetics arises. Moreover, in the case of dental prostheses such as ceramic inlays, all ceramic crowns, resin facing crowns, and porcelain facing metal crowns, since a high-level technique is required for building up and forming through porcelain works, there is a defect that not only a lot of skill by a dental technician but also a long period of time and much expenses are required.

On the other hand, Japanese Patent Laid-Open No. 227400/1995 discloses a process for preparing a denture base by charging under a high pressure a thermoplastic resin, a thermosetting resin, etc. into in a mold, in which a process for preparing a dental prosthesis such as an inlay and a crown is also described. This process is a process in which a denture base is subjective and is formed by charging under a high pressure a thermoplastic resin into a mold, with thermoplastic resins having good fluidity, such as polycarbonates, polysulfones, polyethersuflones, and acrylic resins, being used. However, even when these thermoplastic resins are compounded and reinforced with glass fibers, etc., the strength is still insufficient. Accordingly, it was hard to say that these thermoplastic resins have a performance sufficient for utilizations of the preparation of dental prostheses such as crowns, which are required to have a mechanical strength and wearing durability.

SUMMARY OF THE INVENTION

The invention is aimed to provide a process for preparing a dental prosthesis, particularly suitable for an inlay, a crown, etc., which is not only superior in aesthetics and mechanical properties but also is free from any fear of pulp irritation by unpolymerized monomers.

We, the present inventors, investigated that when, by applying a technique of injection molding or pressure injection, which has hitherto been employed for the preparation of dentures, artificial teeth, etc., a composite resin having a superior strength as compared with thermoplastic resins such as polysulfones and being, superior in esthetics to metal materials, is charged under pressure into a mold and subjected to polymerization under heat and pressure, a dental prosthesis that is free from the remaining of unpolymerized monomers and superior in mechanical properties can be prepared, leading to the accomplishment of a process for preparing a dental prosthesis according to the invention.

Specifically, the invention is to provide a process for preparing a dental prosthesis comprising preparation of a wax pattern of an objective dental prosthesis based on a duplicated model having an intraoral shape, investment of the wax pattern in an investment material, and removal of the wax pattern to prepare a mold, wherein a composite resin is charged under pressure into the mold, and the composite resin is cured under heat and pressure.

DESCRIPTION OF THE PREFERRED EMBODIMENTS

In carrying out the process for preparing a dental prosthesis according to the invention, first of all, a tooth on which an objective dental prosthesis is applied subjected to preparation of a cavity or core construction of the tooth, and an impression of its shape is then taken by using a dental impression material, etc. At this time, any materials can be used without particular limitations as the impression material to be used, so far as they can preciously reproduce the shape of the tooth. However, impression materials that are popularly used in the dentistry field are preferred because they are superior in precision and handling, with dental silicone impression materials being particularly preferred.

Subsequently, a dental gypsum, a dental investment or the like is poured into the taken impression and set to prepare a duplicated model having an intraoral shape. Then, a wax such as a dental wax is applied on the duplicated model to prepare a wax pattern of an objective dental prosthesis, and the thus completed wax pattern is attached to a sprue made of a wax or a metal in a usual manner.

Subsequently, the wax pattern is invested, either alone or together with a duplicated model, in a heat-resistant vessel such as a casting ring, by using an investment material. As the investment material, in the case where the viscosity of the composite resin to be charged under pressure is low, and the maximum charging pressure is low as 0.5 to 5 MPa, casting investment materials that are used in the dentistry can be used. Further, when a dental gypsum or the like is used, it is possible to apply a higher pressure. Moreover, in the case where a charging pressure exceeding 5 MPa is required, it is preferred to use a dental improved stone that is durable to a higher pressure.

After setting of the investment material, the whole of the heat-resistant vessel is heated according to a customary manner, and the internal wax pattern is removed to prepare a mold. When the wax pattern cannot be burnt and removed by burning as in the case where a gypsum is used as the investment material, the wax is removed by using hot water or upon heating in an air pressure pot to prepare a mold.

Thereafter, the heat-resistant vessel is set on a pressure injection apparatus, and a composite resin is charged under pressure thereinto. The charging pressure is 0.5 to 30 MPa, and preferably 5 to 20 MPa. When the charging pressure is lower than 0.5 MPa, the composite resin may not spread into details of the mold. In contrast, when it exceeds 30 MPa, the cast and the dental gypsum for investment are in danger of breakage.

In the case where it is difficult to charge under pressure the composite resin because of its high viscosity, it is possible to charge under pressure the composite resin after softening the composite resin upon heating at 60 to 90° C. and further heating the heat-resistant vessel at 120 to 150° C. to adjust the fluidity. When the temperature at the time of charging under pressure is lower than 60° C., the effect for increasing the fluidity cannot be obtained. In contrast, in the case that the temperature exceeds 90° C., the polymerization and curing of the composite resin are rapidly promoted, there is a possibility of the polymerization and curing to occur before the charging under pressure, and hence, such is not preferred.

At the time of charging under pressure, in order that the composite resin spreads into the details without causing the breakage of the investment material, it is necessary to adjust the time, pressure and temperature of the charging under pressure of the composite resin.

After the charging under pressure, the composite resin is pressurized and heated to effect polymerization and curing. At the time of the pressurization and heating, it is preferred that the pressure is about 70 to 100% of that upon charging under pressure, whereas the heating temperature is from 95 to 150° C.

The time of the pressurization and heating varies depending upon the pressurization and heating conditions and the polymerization properties of monomers or oligomers to be used for the composite resin, such as (meth)acrylates, but it is usually 2 to 30 minutes, and preferably 5 to 15 minutes.

After pressurizing and heating the composite resin to effect polymerization and curing, the composite resin is cooled as it is in a pressurized state and then reduced in the pressure. The retention of the pressure is necessary for spreading the composite resin into the details of the dental prosthesis as well as correcting the polymerization shrinkage of the composite resin.

As the apparatus for charging under pressure, an apparatus for charging under pressure, which is usually used in the dentistry, and in which a dental material for denture base used for the preparation of a denture base or the like can be charged into a pressure-resistant vessel under a pressure of 0.5 to 30 MPa, can be used.

The composite resin that is used in the invention is a composite resin comprising a (meth)acrylate arbitrarily compounded with one or more than two inorganic, organic or inorganic-organic composite fillers and further added with a heat polymerization catalyst. Namely, the composite resin used in the invention is compounded with a heat polymerization catalyst suitable for the heat polymerization under pressure and adjusted so as to be suited for the charging under pressure instead of a light-polymerization catalyst for dental composite resins, which has hitherto been used mainly for filling and restoration in the dentistry.

As the (meth) acrylate, those which are generally used for the dental composite resin can be used, and in addition to monomers, oligomers and the like can be used. Examples of monomers include methyl methacrylate, ethyl methacrylate, isopropyl methacrylate, 2-hydroxyethyl methacrylate, 3-hydroxypropyl methacrylate, 2-hydroxy-1,3-dimethacryloxypropane, n-butyl methacrylate, isobutyl methacrylate, hydroxypropyl methacrylate, tetrahydrofurfuryl methacrylate, glycidyl methacrylate, 2-methoxyethyl methacrylate, 2-ethylhexyl methacrylate, benzyl methacrylate, ethylene glycol dimethacrylate, diethylene glycol dimethacrylate, triethylene glycol dimethacrylate, tetraethylene glycol dimethacrylate, neopentyl glycol dimethacrylate, 1,3-butylene glycol dimethacrylate, 1,4-butylene glycol dimethacrylate, 1,6-hexanediol dimethacrylate, trimethylolpropane trimethacrylate, trimethylolethane trimethacrylate, tetraethylene glycol dimethacrylate, pentaerythritol trimethacrylate, trimethylolmethane trimethacrylate, pentaerythritol tetramethacrylate, di-2-methacryloxyethyl-2,2,4-trimethyl hexamethylene dicarbamate, 1,3,5-tris[1,3-bis(methacryloyloxy)-2-propoxycarbonylaminohexane]-1,3,5-(1H,3H,5H)-triazine-2,4,6-trione, 1,6-methacrylethyloxycarbonylaminohexane, 1,3-methacrylethyloxycarbonylaminohexylaminocarbonyloxy (3-methyl)propane, and 1,6-methacrylethyloxycarbonylaminohexylaminocarbonyloxy (3-methyl)propyloxycarbonylaminohexane, as well as corresponding acrylates thereto. Further, examples of oligomers include a urethane oligomer comprising 1,3-butylene glycol, hexamethylene diisocyanate and 2-hydroxyethyl methacrylate and a urethane oligomer comprising 2,2-di (4-hydroxycyclohexyl)propane, hexamethylene diisocyanate and 2-hydroxyethyl methacrylate, as well as corresponding acrylates thereto. These monomers or oligomers can be used singly or in admixture of two or more thereof.

Examples of the filler include various glasses such as barium glass, alumina glass and potassium glass, and powders of silica, feldspar, and quartz. Further, inorganic-organic composite fillers obtained by mixing a monomer with an inorganic filler and curing the mixture, followed by pulverization, can also be used. These fillers are preferably subjected in advance to surface processing with a silane substance, and the surface processing is carried out by a known silane processing process.

Of these, a composite resin containing 30 to 80% by weight, and preferably 60 to 80% by weight of at least one filler selected from a glass powder having a mean particle size of 0.02 to 10 µm, ultrafine powdered silica having a mean particle size of 0.02 to 0.04 µm, and an inorganic-organic composite filler obtained by mixing a monomer with ultrafine powdered silica having a mean particle size of 0.02 to 0.04 μm and curing the mixture, followed by pulverization, is particularly preferred because the strength and the abrasion resistance after curing are high, and the viscosity is suitable for charging under pressure into the mold when the temperature is 60 to 90° C.

As the heat polymerization catalyst are preferred azo compounds such as azobisisobutyronitrile and organometallic compounds such as tributylboron. Further, diacyl peroxides containing an aromatic ring and peroxy esters that are seemed to be an ester of perbenzoic acid, such as benzoyl peroxide, 2,4-dichlorobenzoyl peroxide, m-tolyl peroxide, t-butyl peroxybenzoate, di-t-butyl peroxyisophthalate, 2,5-di-methyl-2,5-di(benzoyl peroxy)hexane, and 2,5-di-methyl-2,5-di[(o-benzoyl)benzoyl peroxy]hexane, can be used.

These heat polymerization catalysts can be used singly or in admixture of two or more thereof. When a compounding amount of the heat polymerization catalyst is less than 0.03% by weight to the composition, a sufficient effect is hardly obtained. In contrast, while varying depending upon the type and compounding amount of the monomer used, when the heat polymerization catalyst is compounded in an amount exceeding 3% by weight, the polymerization reaction proceeds before the heating will be carried out sufficiently, whereby the composite resin may not be charged under pressure into the mold.

With respect to the composite resin used in the invention, in the case where the compounding amount of the ultrafine powdered silica exceeds 10% by weight, since the flow of the paste charged and the discharge of porosities become poor, an air vent for exhaust maybe provided in the investment material, if desired. Further, while the composite resin used in the invention is usually colored into a tooth crown color and used for the preparation of a dental prosthesis such as an inlay and a crown, it is also possible to prepare a denture base having a higher strength by coloring it into a gingival color.

As the heat-resistant vessel surrounding the mold and to be installed on the pressure injection apparatus, a dental flask, which is used for the preparation of a denture in the dentistry, and the like can be used, in addition to the above-described casting ring. In the case where the dental flask is used, the investment is carried out according to a method for use of the investment of a wax pattern using a dental flask, which is generally employed in the preparation of a denture, and the installation of a sprue is carried out, and then, the composite resin is charged under pressure according to the method as described above.

In the case where the dental flask is of a separation type, since the sprue is set along the gypsum and investment from the wax pattern to the composite resin inlet, it is preferred that the cross-sectional shape of the sprue is rectangular, half-round, etc. As a method for the removal of the wax pattern, a method in which the vessel is once separated, the wax pattern is subjected to complete wax removal by using hot water, etc., and then, the heat-resistant vessel is again assembled, is suitable.

In the case where a dental flask is used as the heat-resistant vessel, and a dental improved stone is used as the investment material, a pressure over 10 MPa can be applied. Accordingly, it is possible to improve the strength and abrasion resistance of the composite resin after the polymerization.

According to the process of the invention, dental prostheses such as inlays and crowns, which are superior in aesthetics and mechanical properties and free from pulp irritation by the unpolymerized monomer, can be easily prepared. As a matter of course, the process of the invention can be applied to the preparation of a denture base.

The process for preparing a dental prosthesis according to the invention will be described more specifically with reference to the following Examples.

Tests were carried out with respect to dental prostheses of the following Examples 1 to 4 and Comparative Examples 1 and 2, as prepared by adding 100 parts by weight of each of composite resins having the following compositions with 0.1 part by weight of iron oxide, tri-iron tetroxide, titanium dioxide, chromium oxide, or the like for the purpose of coloring it into a tooth crown color as well as that as prepared by using a commercially available composite resin. The results obtained are summarized and shown in Table 1.

(Composite Resin I)

As the (meth)acrylate:

14.6% by weight of di-2-methacryloxy-2,2,4-trimethyl hexamethylene dicarbamate (hereinafter abbreviated as "UDMA") 5.0% by weight of a mixture (a trade name: Art Resin SH-101, made by Negami Chemical Industrial Co., Ltd., hereinafter abbreviated as "SE-101") consisting of 1,6-methacrylethyloxycarbonylaminohexane, 1,3-methacrylethyloxycarbonylaminohexylaminocarbonyloxy (3-methyl)propane and 1,6-methacrylethyloxycarbonylaminohexylaminocarbonyloxy-(3-methyl)propyloxycarbonylaminohexane; and 5.0% by weight of tetraethylene glycol dimethacrylate (hereinafter abbreviated as "TEGDMA")

As the filler:

45% by weight of colloidal silica having a mean particle size of 0.04 μm as an inorganic filler (a trade name: Aerosil OX-50, made by Nippon Aerosil Corporated, hereinafter abbreviated as "OX-50") and 30% by weight of barium glass having a mean particle size of 0.5 μm as a glass powder As the heat polymerization catalyst:

0.4% by weight of benzoyl peroxide (Composite Resin II)

As the (meth)acrylate:

29.8% by weight of UDMA and 7.0% by weight of SH-101

As the filler:

63% by weight of OX-50 as an inorganic filler

As the heat polymerization catalyst:

0.2% by weight of benzoyl peroxide (Composite Resin III)

As the (meth)acrylate:

16.3% by weight of UDMA and 8.0% by weight of TEGDMA

As the filler:

3% by weight of colloidal silica having a mean particle size of 0.016 μm as an inorganic filler (a trade name: Aerosil R-972, made by Nippon Aerosil Corporated, hereinafter abbreviated as "R-972") and 72% by weight of fluoroaluminosilicate glass as a glass powder (prepared by weighing 25.0 g of alumina, 27.7 g of calcium carbonate, 15.2 g of aluminum phosphate, 13.3 g of aluminum fluoride, and 11.7 g of silica sand, respectively, mixing them with each other, charging the mixture into a platinum crucible, placing the crucible in an electric furnace, elevating the temperature in the furnace to 1,250° C. over about 3 hours to melt the mixture, keeping that temperature for 2 hours to clarify a molten glass, and quenching and pulverizing it to adjust it so as to have a mean particle size of 1.0 μm)

As the heat polymerization catalyst:
  0.7% by weight of benzoyl peroxide
(Composite Resin IV)
As the (meth)acrylate:
  21.3% by weight of UDMA and 10.0% by weight of TEGDMA
As the filler:
  16% by weight of OX-50 as an inorganic filler and 52% by weight of a powder as an inorganic-organic composite filler {prepared by mixing 45% by weight of a powder obtained by subjecting colloidal silica having a mean particle size of 0.04 $\mu$m (a trade name: Aerosil OX-50, made by Nippon Aerosil Corporated) to surface processing with an ethanol solution of 10% by weight of $\gamma$-mehtacryloxypropyl trimethoxysilane in a customary manner, with 55% by weight of a solution of 1 part by weight of 2,2'-azobisisobutyronitrile dissolved in 100 parts by weight of a monomer mixing solution consisting of 19 parts by weight of UDMA, 13 parts by weight of 1,3,5-tris-[1,3-bis(methacryloyloxy)-2-propoxycarbonylaminohexane]-1,3,5-(1H, 3H, 5H) triazine-2,4,6-trione, and 13 parts by weight of neopentyl glycol dimethacrylate, heat curing the mixture, and pulverizing it to adjust it so as to have a mean particle size of 10 $\mu$m}
As the heat polymerization catalyst:
  0.7% by weight of benzoyl peroxide

EXAMPLE 1

(1) A shape of a first molar prepared a class II cavity was subjected to impression taking using a dental silicone impression material in a customary manner, and a dental improved stone (a trade name: New Fujirock, made by GC Corporation) was mixed with water and poured into the impression to prepare a gypsum model.

(2) A wax pattern of an inlay was prepared on the gypsum model by using a dental wax (a trade name: Inlay Wax, made by GC Corporation) and set in an investment flask (a trade name: Acroflask, made by GC Corporation) as a whole including the gypsum model at a position along an axis between an inlet for pouring the resin and an exhaust outlet of the flask. At this time, the bottom surface of the gypsum was inclined and adjusted such that a front surface portion of the wax pattern was exposed as much as possible.

(3) An air vent was prepared along the gypsum model from a portion of the wax pattern that was considered to be most hardly poured with the resin to the vent outlet by using a wax (a trade name: Ready Casting Wax, made by GC Corporation), and the gypsum model was invested in a lower portion of the flask by using a dental improved stone (a trade name: New Fujirock, made by GC Corporation).

(4) After setting the dental improved stone, a sprue was prepared on the wax pattern by using a wax, a separating agent was applied on a surface of the gypsum, an inner lid of the flask was placed thereon, a dental improved stone (a trade name: New Fujirock, made by GC Corporation) was again poured into the flask, and an upper lid was placed thereon to effect investment.

(5) After setting the dental improved stone, the flask was separated, and the wax pattern was subjected to complete removal of the wax by using hot water.

(6) The separated flask was again assembled, fixed firmly with bolts, and then set on a pressure injection apparatus (a trade name: Acropress, made by GC Corporation).

(7) The Composite Resin I colored in a tooth crown color was heated at 80° C. for softening and charged into the flask heated at 130° C. under a maximum pressure of 10 MPa. After keeping the Composite Resin I under heat and pressure at 130° C. and at 8 MPa for 7 minutes, the Composite Resin I was cooled while in a pressurized state and then decreased in the pressure. A molded article obtained from the Composite Resin I was taken out from the mold, and the resins in the sprue and air vent portions were cut away, followed by polishing to obtain a desired inlay.

EXAMPLE 2

A dental prosthesis was prepared in the same manner as in Example 1, except that the Composite Resin II colored in a tooth crown color was heated at 80° C. for softening and charged into the flask heated at 130° C. under a maximum pressure of 23 MPa, and that the Composite Resin II was set under heat at 130° C. and pressure at 20 MPa for 8 minutes.

EXAMPLE 3

(1) A shape of a first molar prepared with a class II cavity was subjected to impression taking using a dental silicone impression material in a customary manner, and a dental improved stone (a trade name: New Fujirock, made by GC Corporation) was mixed with water and poured into the impression to prepare a gypsum model.

(2) A wax pattern of an inlay was prepared on the gypsum model by using a dental wax (a trade name: Inlay Wax, made by GC Corporation) and invested in an investment heating vessel (a trade name: Casting Ring, made by GC Corporation) by using a dental refractory investment (a trade name: Ceravest, made by GC Corporation) in a customary manner.

(3) After setting the dental refractory investment, the investment heating vessel was heated at 700° C., thereby burning out the internal wax pattern to prepare a mold.

(4) The mold heated at about 130° C. was installed on a pressure injection apparatus (a trade name: Acropress, made by GC Corporation). Then, the Composite Resin III colored into a tooth crown color was heated at 70° C. for softening and charged at a pressure of 0.7 MPa, followed by heating and pressuring at 120° C. and at 0.6 MPa to mold.

(5) After maintaining the heat and pressure for 9 minutes, the Composite Resin III was cooled as it was in a pressurized state and then decreased in pressure. A molded article obtained from the Composite Resin III was taken out from the mold, and the resin branches in the sprue portion were cut away, followed by polishing to obtain a desired inlay.

EXAMPLE 4

(1) A shape of a first molar prepared with a class II cavity was subjected to wax removal in a customary manner and in the same manners as in Example 1-(1) to (5).

(2) The flask was firmly fixed with bolts and set on a pressure injection apparatus (a trade name: Acropress, made by GC Corporation).

(3) The Composite Resin IV colored into a tooth crown color was heated at 70° C. for softening and charged in the flask heated at 130° C. under a pressure in the mold of 5 MPa. After keeping the Composite Resin IV under heat and pressure at 130° C. and at 4 MPa for 7 minutes, the Composite Resin IV was cooled while in a pressurized state and then decreased in the pressure. A molded article obtained from the Composite Resin IV was taken out from the mold, and the resins in the sprue and air vent portions were cut away, followed by polishing to obtain a desired inlay.

Comparative Example 1

(1) A shape of a first molar prepared with a class II cavity was subjected to impression taking using a dental silicone impression material in a customary manner, and a dental improved stone (a trade name: New Fujirock, made by GC Corporation) was mixed with water and poured into the impression to prepare a gypsum model.

(2) After applying a separating agent (a trade name: CR Seb, made by Kuraray Co., Ltd.) on the gypsum mold, a dental light-polymerization type Composite Resin V was filled in the cavity and irradiated with light for curing for one minute by means of a light-irradiator (a trade name: New Light VL-II, made by GC Corporation). A cured product was taken out from the gypsum model followed by polishing to obtain a desired inlay.

The composition of the dental Composite Resin V used in this Comparative Example 1 is shown in Table 1. This dental Composite Resin V is the same as the Composite Resin IV, except that camphorquinone and ethyl p-dimethylaminobenzoate were compounded in amounts of 0.2% by weight and 0.5% by weight, respectively in place of the benzoyl peroxide as the heat polymerization catalyst.

Comparative Example 2

An inlay was prepared in the same manner as in Comparative Example 1, except using a commercially available dental light-polymerization type composite resin (a trade name: Graft LCII, made by GC Corporation), which is to be used for restoration by direct filling.

Measurement of the Amount of Remaining Unpolymerized Monomer

A fragment having a thickness of 0.15±0.25 mm was cut out from each of the (dental) composite resins prepared under the polymerization conditions of the Examples and Comparative Examples, weighed, and then immersed in methanol (5 ml) for 24 hours. Thereafter, the elute solution was added with 5 ml of methanol containing 2-ethylhexyl methacrylate as an internal standard sample, and the amount of the monomer was measured by means of high-performance liquid chromatography. Then, the amount of the unpolymerized monomer was calculated from a calibration curve and expressed in terms of a ratio with respect to the weight before immersing.

Diametral Tensile Strength Test

For the diametral tensile strength test, a specimen in a cylindrical shape of 4 mm$\phi$×6 mm was prepared in accordance with each of the methods of the Examples and Comparative Examples and immersed in distilled water at 37° C. for 24 hours. Thereafter, the diametral tensile strength test was carried out at a cross head speed of 1 mm/min. by a testing machine (a trade name: Autograph, made by Shimadzu Corporation).

TABLE 1

| | Composition | | | | | Mechanical properties | |
| --- | --- | --- | --- | --- | --- | --- | --- |
| | | Filler | | | | Amount of | |
| | (Meth) acrylate (% by weight) | Inorganic filler (% by weight) | Inorganic-organic composite filler (% by weight) | Glass powder (% by weight) | Heat polymerization catalyst (% by weight) | remaining unpolymerized Monomer (%) | Diametral tensile strength (MPa) |
| Example 1 | UDMA 14.6<br>SH-101 5.0<br>TEGDMA 5.0 | OX-50 45 | — | Barium glass powder 30 | Benzoyl peroxide 0.4 | Not detected | 466 |
| Example 2 | UDMA 29.8<br>SH-101 7.0 | OX-50 63 | — | — | Benzoyl peroxide 0.2 | Not detected | 571 |
| Example 3 | UDMA 16.3<br>TEGDMA 8.0 | R-972 3 | — | Fluoroalumino-silicate glass powder 72 | Benzoyl peroxide 0.7 | Not detected | 420 |
| Example 4 | UDMA 21.3<br>TEGDMA 10.0 | OX-50 16 | 52 | — | Benzoyl peroxide 0.7 | Not detected | 426 |
| Comparative Example 1 | UDMA 21.3<br>TEGDMA 10.0 | OX-50 16 | 52 | — | Camphorquinone 0.2<br>Ethyl p-dimethylamino-benzoate 0.5 | 1.22 | 385 |
| Comparative Example 2 | Commercially available dental light-polymerization type composite resin (a trade name: Graft LCII, made by GC Corporation) | | | | | 0.96 | 364 |

It can be confirmed from Table 1 that the dental prostheses prepared from the composite resins in Examples 1 to 4 are superior in mechanical properties and free from the unpolymerized monomer, as compared with those in Comparative Examples 1 and 2.

As described above, the present invention provides an epoch-making process for preparing a dental prosthesis, which enables to obtain a dental prosthesis that has suitable esthetics and superior mechanical properties and is free from pulp irritation by the unpolymerized monomer, by charging under pressure a composite resin into a mold and curing it under heat and pressure, and hence, is greatly valuable in contribution to the dental field.

While the present invention has been described in detail and with reference to specific examples thereof, it will be apparent to one skilled in the art that various changes and modifications can be made therein without departing from the spirit and scope thereof.

What is claimed is:

1. A process, comprising
preparing a wax pattern of an objective dental prosthesis based on a duplicated model having an intraoral shape;
investing the wax pattern in an investment material;
removing the wax pattern to prepare a mold;
charging a composite resin into the mold under a pressure of from 0.5 to 30 MPa and at a temperature of from 60 to 90° C.; and
curing the composite resin under heat and pressure, wherein the composite resin comprises a (meth) acrylate compounded with one or more than two inorganic, organic, or inorganic-organic composite fillers and further with a heat polymerization catalyst.

2. The process according to claim 1, wherein the composite resin comprises from 30 to 80% by weight of at least one filler selected from a group consisting of glass powder having a mean particle size of 0.02 to 10 $\mu$m, ultrafine powdered silica having a mean particle size of 0.02 to 0.04 $\mu$m, and an inorganic-organic composite filler obtained by mixing a monomer with ultrafine powdered silica having a mean particle size of 0.02 to 0.04 $\mu$m and curing the mixture, followed by pulverization.

3. The process according to claim 1, wherein the curing is performed under a pressure that is from 70 to 100% of the pressure during charging and a temperature of from 95 to 150° C.

4. The process according to claim 1, wherein the charging is performed under pressure and temperature for a time of from 2 to 30 minutes.

5. The process according to claim 2, wherein the curing is performed under a pressure that is from 70 to 100% of the pressure during charging and a temperature of from 95 to 150° C.

6. The process according to claim 5, wherein the charging is performed under pressure and temperature for a time of from 2 to 30 minutes.

7. The process according to claim 2, wherein the charging is performed under pressure and temperature for a time of from 2 to 30 minutes.

8. The process according to claim 3, wherein the charging is performed under pressure and temperature for a time of from 2 to 30 minutes.

* * * * *